US010925816B2

(12) United States Patent
Lee et al.

(10) Patent No.: US 10,925,816 B2
(45) Date of Patent: Feb. 23, 2021

(54) COMPOSITION FOR TRANSDERMAL DELIVERY, COMPRISING NANOEMULSION AND MODIFIED LAYERED DOUBLE HYDROXIDE

(71) Applicant: H&A PHARMACHEM CO., LTD, Gyeonggi-do (KR)

(72) Inventors: Jong Hyeon Lee, Gyeonggi-do (KR); Se Hee Cho, Seoul (KR); Young Rong Woo, Gangwon-Do (KR); Young Ah Park, Gangwon-Do (KR); Hong Geun Ji, Gyeonggi-do (KR)

(73) Assignee: H&A PHARMACHEM CO., LTD., Gyeonggi-Do (KR)

( * ) Notice: Subject to any disclaimer, the term of this patent is extended or adjusted under 35 U.S.C. 154(b) by 0 days.

(21) Appl. No.: 16/325,483

(22) PCT Filed: Aug. 18, 2017

(86) PCT No.: PCT/KR2017/009058
§ 371 (c)(1),
(2) Date: Feb. 14, 2019

(87) PCT Pub. No.: WO2018/034548
PCT Pub. Date: Feb. 22, 2018

(65) Prior Publication Data
US 2019/0192396 A1    Jun. 27, 2019

(30) Foreign Application Priority Data

Aug. 18, 2016  (KR) .................. 10-2016-0104883

(51) Int. Cl.
*A61K 8/06*       (2006.01)
*A61K 8/34*       (2006.01)
(Continued)

(52) U.S. Cl.
CPC ................ *A61K 8/06* (2013.01); *A61K 8/27* (2013.01); *A61K 8/34* (2013.01); *A61K 8/345* (2013.01);
(Continued)

(58) Field of Classification Search
None
See application file for complete search history.

(56) References Cited

U.S. PATENT DOCUMENTS 5,474,762 A    12/1995  Carr et al.
5,618,545 A *  4/1997  Orita ...................... A61P 43/00
                                                        424/401
(Continued)

FOREIGN PATENT DOCUMENTS

JP    2014-205638     * 10/2014
JP    2014-205638 A    10/2014
(Continued)

OTHER PUBLICATIONS

English translation for JP2014-205638 (2014).*
(Continued)

*Primary Examiner* — Sin J Lee (57) ABSTRACT

The present invention relates to: a composition for transdermal delivery, comprising 1) a nanoemulsion comprising an active ingredient, saturated lecithin, phytosteryl/behenyl/octyldodecyl lauroyl glutamate, a polyol, and water, and 2) a modified layered double hydroxide; and a preparation method therefor.

18 Claims, 7 Drawing Sheets

(51) Int. Cl.
| | |
|---|---|
| A61K 8/68 | (2006.01) |
| A61K 8/97 | (2017.01) |
| A61K 8/64 | (2006.01) |
| A61K 8/67 | (2006.01) |
| A61K 8/73 | (2006.01) |
| A61K 8/9789 | (2017.01) |
| A61K 8/9794 | (2017.01) |
| A61K 8/92 | (2006.01) |
| A61K 8/27 | (2006.01) |
| A61K 8/368 | (2006.01) |
| A61K 8/46 | (2006.01) |
| A61K 8/55 | (2006.01) |
| A61K 8/60 | (2006.01) |
| A61K 8/63 | (2006.01) |
| A61K 9/00 | (2006.01) |
| A61K 9/107 | (2006.01) |
| A61K 31/194 | (2006.01) |
| A61K 31/573 | (2006.01) |
| A61K 47/14 | (2017.01) |
| A61K 47/02 | (2006.01) |
| A61K 47/10 | (2017.01) |
| A61K 47/24 | (2006.01) |
| A61K 47/28 | (2006.01) |
| A61P 29/00 | (2006.01) |
| A61P 5/24 | (2006.01) |
| A61P 17/02 | (2006.01) |
| A61P 17/00 | (2006.01) |
| A61P 17/14 | (2006.01) |
| A61P 31/04 | (2006.01) |
| A61P 3/02 | (2006.01) |
| A61Q 19/00 | (2006.01) |
| A61Q 7/00 | (2006.01) |
| A61Q 17/04 | (2006.01) |
| A61Q 19/02 | (2006.01) |

(52) U.S. Cl.
CPC .............. *A61K 8/368* (2013.01); *A61K 8/463* (2013.01); *A61K 8/55* (2013.01); *A61K 8/553* (2013.01); *A61K 8/60* (2013.01); *A61K 8/63* (2013.01); *A61K 8/64* (2013.01); *A61K 8/67* (2013.01); *A61K 8/68* (2013.01); *A61K 8/73* (2013.01); *A61K 8/735* (2013.01); *A61K 8/92* (2013.01); *A61K 8/922* (2013.01); *A61K 8/97* (2013.01); *A61K 8/9789* (2017.08); *A61K 8/9794* (2017.08); *A61K 9/0014* (2013.01); *A61K 9/107* (2013.01); *A61K 9/1075* (2013.01); *A61K 31/194* (2013.01); *A61K 31/573* (2013.01); *A61K 47/02* (2013.01); *A61K 47/10* (2013.01); *A61K 47/14* (2013.01); *A61K 47/24* (2013.01); *A61K 47/28* (2013.01); *A61P 3/02* (2018.01); *A61P 5/24* (2018.01); *A61P 17/00* (2018.01); *A61P 17/02* (2018.01); *A61P 17/14* (2018.01); *A61P 29/00* (2018.01); *A61P 31/04* (2018.01); *A61Q 7/00* (2013.01); *A61Q 17/04* (2013.01); *A61Q 19/00* (2013.01); *A61Q 19/007* (2013.01); *A61Q 19/02* (2013.01); *A61K 2800/413* (2013.01)

(56) References Cited

U.S. PATENT DOCUMENTS

| | | | | |
|---|---|---|---|---|
| 2001/0051169 | A1* | 12/2001 | Saint-Leger | A61P 17/00 424/401 |
| 2004/0171735 | A1* | 9/2004 | Choy | A61K 8/02 524/500 |
| 2011/0240050 | A1* | 10/2011 | Perruna | A61K 8/361 132/200 |
| 2015/0368811 | A1* | 12/2015 | Gray | C25B 1/04 205/630 |
| 2017/0044421 | A1* | 2/2017 | Parvulescu | C09K 8/58 |
| 2017/0281510 | A1* | 10/2017 | Kobayashi | A61K 8/34 |

FOREIGN PATENT DOCUMENTS

| | | |
|---|---|---|
| KR | 10-2004-0063878 A | 7/2004 |
| KR | 10-2011-0028981 A | 3/2011 |
| KR | 10-2013-0042056 A | 4/2013 |
| KR | 10-2014-0067748 A | 6/2014 |
| KR | 10-2014-0117042 A | 10/2014 |
| WO | WO-2014/168095 A1 | 10/2014 |

OTHER PUBLICATIONS

English translation for WO 2014/168095 A1 (Imaizumi) (2014).*
International Search Report from corresponding PCT Application No. PCT/KR2017/009058, dated Nov. 24, 2017.
Extended European Search Report from corresponding European Patent Application No. 17841730.9, dated Feb. 21, 2020.
Wang, J. et al., "Double Phase Inversion of Emulsions Containing Layered Double Hydroxide Particles Induced by Adsorbtion of Sodium Dodecyl Sulfate", Langmuir 2008, 24, pp. 10054-10061.

* cited by examiner

COMPOSITION FOR TRANSDERMAL DELIVERY, COMPRISING NANOEMULSION AND MODIFIED LAYERED DOUBLE HYDROXIDE

CROSS-REFERENCE TO RELATED APPLICATIONS

This application is a national phase application of PCT Application No. PCT/KR2017/009058, filed on 18 Aug. 2017, which claims benefit of Korean Patent Application No. 10-2016-0104883, filed on 18 Aug. 2016. The entire disclosures of the applications identified in this paragraph are incorporated herein by references.

FIELD

The present invention relates to a composition for transdermal delivery comprising: 1) a nanoemulsion comprising an active ingredient, saturated lecithin, phytosteryl/behenyl/octyldodecyl lauroyl glutamate, a polyol and water; and 2) a modified layered double hydroxide.

In addition, the present invention relates to a personal care composition comprising the composition for transdermal delivery.

Furthermore, the present invention relates to a method for preparing a composition for transdermal delivery comprising: i) mixing an active ingredient, saturated lecithin, phytosteryl/behenyl/octyldodecyl lauroyl glutamate, a polyol and water, and preparing a nanoemulsion; and ii) mixing the nanoemulsion prepared in step (i) and a modified layered double hydroxide to obtain a complex.

BACKGROUND

To stabilize an active ingredient and increase transdermal efficiency, efforts and study for utilizing a transdermal delivery system to functional cosmetics have been actively carried out. Because of developing functional materials, various functionalization methods for imparting higher stability to such materials have been widely studied. Specifically, it is well known that light, heat and oxygen in the air seriously reduce the biological activity of functional materials. As such, there is a need to develop a new functionalization technique for stabilizing various active ingredients.

Stratum corneum-which presents the outmost of the skin—is a primary protection membrane playing a role of barrier function. In stratum corneum, corneocytes form a shape as laying bricks, and intercorneocyte lipids play a role as mortar supporting these corneocytes. This lipid layer is highly structurized, and plays an important role in the barrier function of stratum corneum. Many methods have been used to absorb materials across stratum corneum. First, the application region for applying to the skin is widened. Second, the permeability of the skin is increased. Third, materials are activated to increase force for moving independently. In the case that active ingredients cannot move due to their large molecular size or the barrier property of stratum corneum must be overcome, the use of a method via a transdermal route may be helpful for resolving such problems.

As a carrier for transdermal absorption, for example Korean Patent Application Publication No. 10-2013-0042056 discloses a cosmetic composition containing carotenoid, a collagen having an average molecular weight of 40,000 or more, and a collagen peptide having a weight average molecular weight of from 200 to 5,000, and Korean Patent Application Publication No. 10-2014-0067748 discloses a drug delivery system for transdermal absorption prepared by dispersing lecithin in an alcohol mixture including propylene glycol.

SUMMARY

Technical Problem

Therefore, the technical problem of the present invention is the provision of a transdermal delivery system which can efficiently deliver an active ingredient into the skin in a stable manner.

In addition, another technical problem of the present invention is the provision of a personal care composition comprising the transdermal delivery system.

Furthermore, still another technical problem of the present invention is the provision of a method for effectively preparing the transdermal delivery system.

Solution to Problem

To solve the above technical problem, the present invention provides a composition for transdermal delivery comprising: 1) a nanoemulsion comprising an active ingredient, saturated lecithin, phytosteryl/behenyl/octyldodecyl lauroyl glutamate, a polyol and water; and 2) a modified layered double hydroxide.

In addition, the present invention provides a personal care composition comprising the composition for transdermal delivery.

Furthermore, the present invention provides a method for preparing a composition for transdermal delivery comprising: i) mixing an active ingredient, saturated lecithin, phytosteryl/behenyl/octyldodecyl lauroyl glutamate, a polyol and water, and preparing a nanoemulsion; and ii) mixing the nanoemulsion prepared in step (i) and a modified layered double hydroxide to obtain a complex.

The present invention is described in detail hereinafter.

According to one aspect to the present invention, a composition for transdermal delivery comprising: 1) a nanoemulsion comprising an active ingredient, saturated lecithin, phytosteryl/behenyl/octyldodecyl lauroyl glutamate, a polyol and water; and 2) a modified layered double hydroxide is provided.

In the present invention, an active ingredient is primarily stabilized by forming a nanoemulsion in the use of saturated lecithin, phytosteryl/behenyl/octyldodecyl lauroyl glutamate, a polyol and water.

The nanoemulsion according to the present invention comprises an active ingredient preferably in an amount of 1 to 40% by weight, and more preferably 5 to 30% by weight. In the present invention, if the amount of the active ingredient is less than 1% by weight, the efficacy according to an active ingredient may be weak, and if the amount of an active ingredient is more than 40% by weight, it may be problematic in the formation of nanoemulsion.

In the present invention, there is no special limitation according to an active ingredient. In the present invention, examples of an active ingredient include, but are not limited to, one or more selected from a moisturizer, a whitening agent, an anti-wrinkle agent, a UV blocking agent, a hair growth promoter, vitamin or a derivative thereof, amino acid or peptide, an anti-inflammatory agent, an acne therapeutic agent, a microbicide, female hormone, a keratolytic agent and a natural product.

Examples of moisturizer include, but are not limited to, creatine, polyglutamic acid, sodium lactate, hydroproline, 2-pyrrolidone-5-carboxyclic acid sodium salt, hyaluronic acid, sodium hyaluronate, ceramide, phytosteryl, cholesterol, sitosterol, pullulan and proteoglycan. Examples of whitening agent include, but are not limited to, arbutin and a derivative thereof, kojic acid, bisabolol, niacinamide, vitamin C and a derivative thereof, placenta and allantoin. Examples of anti-wrinkle agent include, but are not limited to, retinol, retinol derivative, adenosine, licorice extract, red ginseng extract and ginseng extract. Examples of UV blocking agent include, but are not limited to, benzophenone derivative, para-aminobenzoic acid derivative, methoxycinnamic acid derivative and salicylic acid derivative. There is no special limitation to a hair growth promoter, but it may be preferably a blood circulation promoter and/or a hair follicle stimulant. Examples of blood circulation promoter include, but are not limited to, the extract of *Swertia japonica* Makino, cepharanthin, vitamin E and a derivative thereof and gamma-oryzanol, and examples of hair follicle stimulant include, but are not limited to, capsicum tincture, ginger tincture, cantharides tincture and nicotinic acid benzyl ester. Examples of vitamin or a derivative thereof include, but are not limited to, vitamin A (retinol) and a derivative thereof, vitamin B1, vitamin B2, vitamin B6, vitamin E and derivatives thereof, vitamin D, vitamin H, vitamin K, pantothenic acid and derivatives thereof, biotin, panthenol, coenzyme $Q_{10}$ and idebenone. Examples of amino acid or peptide include, but are not limited to, cysteine, methionine, serine, lysine, tryptophan, amino acid extract, epidermal growth factor (EGF), insulin-like growth factor (IGF), fibroblast growth factor (FGF), copper tripeptide-1, tripeptide-29, tripeptide-1, acetyl hexapeptide-8, nicotinoyl tripeptide-35, hexapeptide-12, hexapeptide-9, palmitoyl pentapeptide-4, palmitoyl tetrapeptide-7, palmitoyl tripeptide-29, palmitoyl tripeptide-1, nonapeptide-7, tripeptide-10 citrulline, sh-polypeptide-15, palmitoyl tripeptide-5, diaminopropionoyl tripeptide-33 and r-spider polypeptide-1. Examples of anti-inflammatory agent include, but are not limited to, beta-glycyrrhetinic acid, glycyrrhetinic acid derivative, aminocaproic acid, hydrocortisone, β-glucan and licorice. Examples of acne therapeutic agent include, but are not limited to, estradiol, estrogen, ethinyl estradiol, triclosan and azelaic acid. Examples of microbicide include, but are not limited to, benzalkonium chloride, benzethonium chloride and halocalban. There is no special limitation to female hormone, but it may be preferably estrogen. As estrogen, it may be preferably estradiol, ethinyl estradiol or isoflavone which is a phytoestrogen. Examples of keratolytic agent include, but are not limited to, sulfur, salicylic acid, AHA, BHA and resorcin. Examples of the extract of natural product or an ingredient obtained therefrom include, but are not limited to, the extract of Japanese witch-hazel, *Lamium album* var. *barbatum, Hedyotis diffusa, Rheum palmatum*, licorice, aloe, chamomile, rose hip, horse chestnut, ginseng, *Luffa aegyptiaca*, cucumber, laver, sea mustard, *Dioscorea batatas*, snail and fruit of *Dioscorea polystachya*, or hinokitiol and beta-carotene. In addition, yeast extract, collagen, elastin, DHA, EPA, flavor ingredient and the like may be used.

The nanoemulsion of the present invention comprises saturated lecithin preferably in an amount of 0.1 to 20% by weight and more preferably 0.2 to 15% by weight. Lecithin refers to a mixture of various phospholipids, and the composition of phospholipids may vary according to origin. Saturated lecithin may be prepared by hydrogenation of lecithin in which all double bonds in hydrocarbons of fatty acids are changed to single bonds. In the present invention, if the amount of saturated lecithin is less than 0.1% by weight, it may be problematic in the formation of nanoemulsion, and if the amount of saturated lecithin is more than 20% by weight, the effect according to the nanoemulsion of the present invention may be insufficient by decreasing the amount of an active ingredient entrapped in nanoemulsion due to an excess of membrane ingredients.

The nanoemulsion of the present invention comprises phytosteryl/behenyl/octyldodecyl lauroyl glutamate as a co-emulsifier preferably in an amount of 0.1 to 20% by weight and more preferably 0.2 to 15% by weight. Phytosteryl/behenyl/octyldodecyl lauroyl glutamate is a mixed ester of phytosterol, behenyl alcohol and octyldodecanol with lauroyl glutamic acid. In the present invention, saturated lecithin only may be insufficient to perfectly form the bilayer membrane of liposome, and so phytosteryl/behenyl/octyldodecyl lauroyl glutamate is used as a co-emulsifier to increase the stability of nanoemulsion. In the present invention, if the amount of phytosteryl/behenyl/octyldodecyl lauroyl glutamate is less than 0.1% by weight or more than 20% by weight, it may be problematic in the formation of nanoemulsion.

The nanoemulsion of the present invention comprises a polyol preferably in an amount of 2 to 70% by weight and more preferably 3 to 65% by weight. In the present invention, a polyol can help the dissolution of an active ingredient. In the present invention, examples of polyol include, but are not limited to, glycerin, sorbitol, xylitol, erythritol, fructose, lactose, mannitol, glucose, sucrose, maltose, maltitol, ethylene glycol or a mixture thereof. If the amount of polyol is less than 2% by weight, it may be problematic in the dissolution of an active ingredient, and if the amount of polyol is more than 70% by weight, it may be problematic in the formation of nanoemulsion.

The nanoemulsion of the present invention comprises water preferably in an amount of 10 to 80% by weight and more preferably 15 to 75% by weight.

The nanoemulsion of the present invention may further comprise vegetable oil. In the present invention, vegetable oil may help the stability of nanoemulsion. In the present invention, examples of vegetable oil include, but are not limited to, olive oil, macadamia oil, sunflower seed oil, camellia oil, castor oil, jojoba oil, almond oil, apricot kernel oil, green tea oil, meadowfoam seed oil, argan oil or a mixture thereof. The nanoemulsion of the present invention comprises vegetable oil preferably in an amount of 10 to 30% by weight and more preferably 12 to 25% by weight. If the amount of vegetable oil is less than 10% by weight, the effect on helping the stability of nanoemulsion may be weak, and if the amount of vegetable oil is more than 30% by weight, it may be problematic in the formation of nanoemulsion.

In the present invention, an active ingredient is secondarily stabilized by forming a complex—in which the nanoemulsion is mixed with a modified layered double hydroxide (LDH) and adsorbed into the interlayer regions of LDH—to obtain a composition for transdermal delivery.

LDH is an inorganic compound having a layered structure, and its composition can be represented by the formula, $[M^{2+}_{1-x} M^{3+}_x(OH)_2]^{x+}(A^{n-})_{x/n} \cdot mH_2O$. In the formula, $M^{2+}$ and $M^{3+}$ are metal cations which locate octahedral sites of brucite; $A^{n-}$ represents anions located between layers; $M^{2+}=Ca^{2+}, Mg^{2+}, Zn^{2+}, Ni^{2+}, Mn^{2+}, Co^{2+}, Fe^{2+}$ and the like; $M^{3+}=Al^{3+}, Cr^{3+}, Mn^{3+}, Fe^{3+}, Ga^{3+}, Co^{3+}, Ni^{3+}$ and the like; $A^{n-}$ is $OH^-, F^-, Cl^-, Br^-, I^-, NO_3^-, CO_3^{2-}, SO_4^{2-}$ and the like; $0.2 \leq x \leq 0.33$ in a fixed-composition phase; and m is usually between 0.5 and 4.

Figure 1:
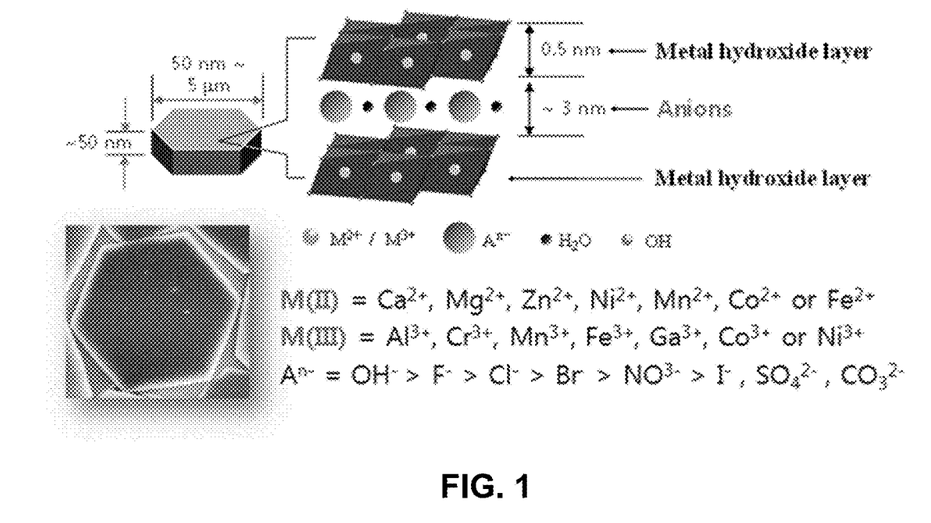
FIG. 1 is a scheme representing the layered structure and composition of layered double hydroxide (LDH).

The anions located in the interlayer regions can be replaced easily, so that even biomolecules such as collagen tripeptide and solid nanoparticle containing Ag, Au, Pt and the like as well as halogen ion and bio-macromolecules having negative charge such as DNA can be intercalated. The basic layered structure of LDH and examples of available metal cations and anions are represented in FIG. 1. The preparation of LDH may be carried out according to the methods known in this technical field such as a hydrothermal method, a convection circulation method, an ultrasonic method and the like.

Meanwhile, the surface functionalization and surface modification may be conducted on the surface of metal hydroxide of LDH with various materials. In the present invention, the surface of LDH is preferably modified with dodecyl sulfate. In one embodiment of the present invention, dodecyl sulfate-modified LDH is exfoliated to a nanosheet form.

A composition for transdermal delivery of the present invention comprises the nanoemulsion and modified layered double hydroxide preferably in an amount of 30 to 70% by weight and more preferably 40 to 60% by weight, respectively.

According to another aspect of the present invention, a personal care composition comprising the composition for transdermal delivery is provided.

In the present invention, examples of personal care composition include, but are not limited to, a skin care composition, a body care composition or a hair care composition. The personal care composition comprises preferably 1 to 60% by weight of the composition for transdermal delivery according to the present invention. In the present invention, if the personal care composition comprises the composition for transdermal delivery in an amount of less than 1% by weight, the effect according to an active ingredient may be weak, and if the amount of the composition for transdermal delivery is greater than 60% by weight, it may be economically undesirable since increasing the effect according to an active ingredient commensurately with the added amount would not be expected.

According to still another aspect of the present invention, a method for preparing a composition for transdermal delivery comprising: i) mixing an active ingredient, saturated lecithin, phytosteryl/behenyl/octyldodecyl lauroyl glutamate, a polyol and water, and preparing a nanoemulsion; and ii) mixing the nanoemulsion prepared in step (i) and a modified layered double hydroxide to obtain a complex is provided.

In step (i) of the preparation method, preferably 1 to 40% by weight of an active ingredient, 0.1 to 20% by weight of saturated lecithin, 0.1 to 20% by weight of phytosteryl/behenyl/octyldodecyl lauroyl glutamate, 2 to 70% by weight of a polyol and 10 to 80% by weight of water, and more preferably 5 to 30% by weight of an active ingredient, 0.2 to 15% by weight of saturated lecithin, 0.2 to 15% by weight of phytosteryl/behenyl/octyldodecyl lauroyl glutamate, 3 to 65% by weight of a polyol and 15 to 75% by weight of water are mixed to prepare a nanoemulsion.

In step (ii) of the preparation method, preferably 30 to 70% by weight of a nanoemulsion and 30 to 70% by weight of a modified layered double hydroxide, and more preferably 40 to 60% by weight of a nanoemulsion and 40 to 60% by weight of a modified layered double hydroxide are mixed to adsorb nanoemulsion into interlayers of modified layered double hydroxide to obtain a composition for transdermal delivery.

Effects of Invention

A composition for transdermal delivery according to the present invention can show excellent efficacy even with a small amount of an active ingredient by increasing bioavailability in which an active ingredient is efficiently transferred into the skin in a very stable form.

DETAILED DESCRIPTION

Hereinafter, the present invention is explained in more detail with the following examples. However, it must be understood that the protection scope of the present invention is not limited to the examples.

Preparation Example 1: Preparation of Layered Double Hydroxide (LDH)

1-1: Synthesis of ZnAl-Carbonate LDH (c-LDH)

ZnAl-LDH containing carbonate ion was synthesized by co-precipitation as follows. 1 M $Na_2CO_3$ solution was slowly added to the mixed solution of 0.2 M $Zn(NO_3)_2$ and 0.1 M $Al(NO_3)_3$ until the final pH became about 7.0. The mixed solution was kept at an about 70° C. oven for a day, filtered, washed with distilled water and ethanol, and dried by the use of a vacuum pump. The formula of the synthesized c-LDH is as follows: $[Zn_4Al_2(OH)_{12}]CO_3 \cdot xH_2O$.

1-2: Synthesis of ZnAl-Carbonate LDH (SA-LDH) in which Surface is Treated with Stearic Acid (SA)

100 g of ZnAl-carbonate LDH and 3 g of stearic acid were dissolved in 100 ml of distilled water, and the mixed solution was stirred at 80° C. for 2 hours. The resulting mixture was filtered, washed with distilled water and ethanol, and dried by the use of a vacuum pump.

1-3: Synthesis of CaAl LDH (DS-LDH) in which Surface is Treated with Dodecyl Sulfate (DS)

$CaCl_2$ and sodium dodecyl sulfate were mixed in a molar ratio of 1:1 and precipitated to obtain a primary material of calcium dodecyl sulfate. The obtained primary material and Al(NO$_3$)$_3$ were mixed in a molar ratio of 2:1, and about 50% by weight of NaOH was added thereto to adjust the pH of the solution to 13. The reaction solution was introduced to a hydrothermal reactor, and the reaction was carried out at 85° C. for a day. The precipitate was filtered, washed with hot distilled water and dried by the use of a vacuum pump. In addition, the reaction solution was introduced to a flask and stirred at about 85° C. for the synthesis, and an ultrasonic device was also used for the synthesis. The formula of the synthesized DS-LDH is as follows: [Ca$_2$Al(OH)$_6$]dodecylsulfate xH$_2$O.

1-3: Synthesis of DS-LDH Nanosheet

For the preparation of LDH nanosheet, the obtained c-LDH was substituted with nitrate ion and stirred in 60° C. formamide solution for about 4 days. For the preparation of DS-LDH nanosheet, after adding about 1 g of sodium dodecyl sulfate to 100 ml of the obtained LDH nanosheet solution, the mixture was stirred for about 1 hour, and the obtained precipitate was washed by the use of a centrifuge.

Figure 2:
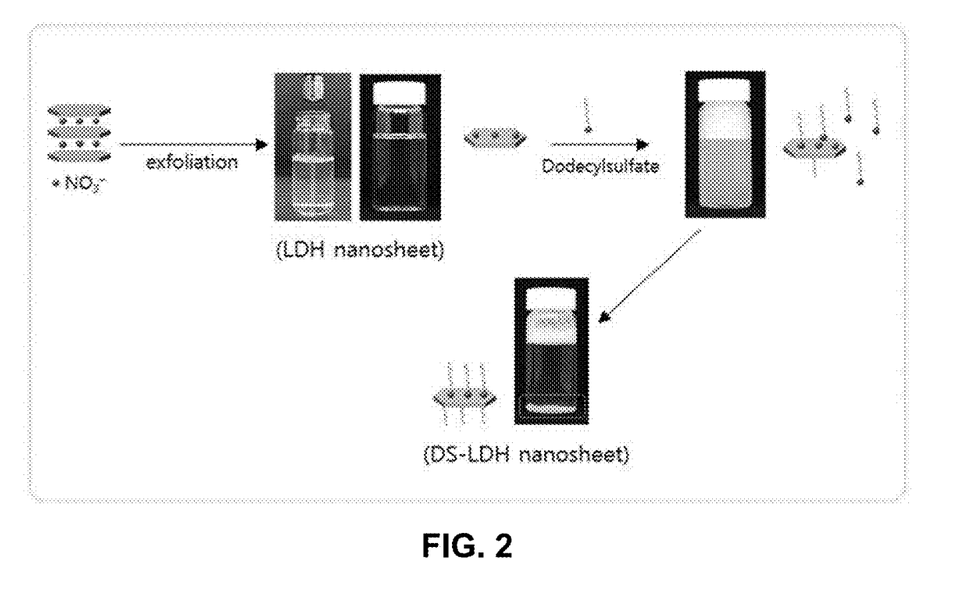
FIG. 2 is a scheme for synthesizing dodecyl sulfate-modified layered double hydroxide (DS-LDH) nanosheet formed by exfoliation of LDH and adsorption of dodecyl sulfate (DS) ion.

FIG. 2 represents a procedure for preparing DS-LDH nanosheet. As can be seen from FIG. 2, LDH nanosheet solution has characteristics of transparency and Tyndall scattering. When sodium dodecyl sulfate, which is a surfactant, is added to a nanosheet solution, a transparent solution is produced by generating electrostatic attraction and hydrogen bond between nanosheets as well as anion substitutions on the surface of LDH nanosheets, and a precipitate is formed according to the elapse of sufficient time.

Preparation Example 2: Preparation of Nanoemulsion Containing Moisturizer

According to the constitutional composition of Table 1, ingredients were introduced to a vessel, dissolved at 50° C. and mixed for 5 minutes by the use of a homo mixer. The resulting mixture was continuously passed five (5) times through a high-pressure microfluidizer at 800 bar, followed by cooling and deaeration to obtain a nanoemulsion containing a moisturizer.

TABLE 1

| Ingredient | Content (% by weight) |
| --- | --- |
| Ceramide 3 | 10 |
| Saturated lecithin | 10 |
| Phytosteryl/behenyl/octyldodecyl lauroyl glutamate | 10 |
| Glycerin | 40 |
| Distilled water | 30 |
| Total amount | 100 |

Preparation Example 3: Preparation of Nanoemulsion Containing Whitening Agent

A nanoemulsion was prepared by the same method as described in Preparation Example 2 except that the constitutional composition of Table 2 was used.

TABLE 2

| Ingredient | Content (% by weight) |
| --- | --- |
| Albutin | 20 |
| Saturated lecithin | 0.5 |
| Phytosteryl/behenyl/octyldodecyl lauroyl glutamate | 0.5 |
| Glycerin | 20 |
| Distilled water | 59 |
| Total amount | 100 |

Preparation Example 4: Preparation of Nanoemulsion Containing UV Blocking Agent

A nanoemulsion was prepared by the same method as described in Preparation Example 2 except that the constitutional composition of Table 3 was used.

TABLE 3

| Ingredient | Content (% by weight) |
| --- | --- |
| Octyl methoxycinnamate | 20 |
| Saturated lecithin | 5 |
| Phytosteryl/behenyl/octyldodecyl lauroyl glutamate | 5 |
| Glycerin | 40 |
| Distilled water | 30 |
| Total amount | 100 |

Preparation Example 5: Preparation of Nanoemulsion Containing Hair Growth Promoter A nanoemulsion was prepared by the same method as described in Preparation Example 2 except that the constitutional composition of Table 4 was used.

TABLE 4

| Ingredient | Content (% by weight) |
| --- | --- |
| Extract of *Swertia japonica* Makino | 20 |
| Saturated lecithin | 5 |
| Phytosteryl/behenyl/octyldodecyl lauroyl glutamate | 1 |
| Sorbitol | 20 |
| Distilled water | 54 |
| Total amount | 100 |

Preparation Example 6: Preparation of Nanoemulsion Containing Vitamin

A nanoemulsion was prepared by the same method as described in Preparation Example 2 except that the constitutional composition of Table 5 was used.

TABLE 5

| Ingredient | Content (% by weight) |
| --- | --- |
| Coenzyme Q$_{10}$ | 10 |
| Saturated lecithin | 5 |
| Phytosteryl/behenyl/octyldodecyl lauroyl glutamate | 5 |
| Glycerin | 40 |

TABLE 5-continued

| Ingredient | Content (% by weight) |
|---|---|
| Olive oil | 20 |
| Distilled water | 20 |
| Total amount | 100 |

Preparation Example 7: Preparation of Nanoemulsion Containing Amino Acid

A nanoemulsion was prepared by the same method as described in Preparation Example 2 except that the constitutional composition of Table 6 was used.

TABLE 6

| Ingredient | Content (% by weight) |
|---|---|
| Cysteine | 5 |
| Saturated lecithin | 1 |
| Phytosteryl/behenyl/octyldodecyl lauroyl glutamate | 5 |
| Erythritol | 20 |
| Distilled water | 69 |
| Total amount | 100 |

Preparation Example 8: Preparation of Nanoemulsion Containing Anti-Inflammatory Agent A nanoemulsion was prepared by the same method as described in Preparation Example 2 except that the constitutional composition of Table 7 was used.

TABLE 7

| Ingredient | Content (% by weight) |
|---|---|
| Hydrocortisone | 5 |
| Saturated lecithin | 1 |
| Phytosteryl/behenyl/octyldodecyl lauroyl glutamate | 5 |
| Glycerin | 30 |
| Distilled water | 59 |
| Total amount | 100 |

Preparation Example 9: Preparation of Nanoemulsion Containing Acne Therapeutic Agent A nanoemulsion was prepared by the same method as described in Preparation Example 2 except that the constitutional composition of Table 8 was used.

TABLE 8

| Ingredient | Content (% by weight) |
|---|---|
| Azelaic acid | 20 |
| Saturated lecithin | 6 |
| Phytosteryl/behenyl/octyldodecyl lauroyl glutamate | 3 |
| Glycerin | 40 |
| Distilled water | 31 |
| Total amount | 100 |

Preparation Example 10: Preparation of Nanoemulsion Containing Natural Product A nanoemulsion was prepared by the same method as described in Preparation Example 2 except that the constitutional composition of Table 9 was used.

TABLE 9

| Ingredient | Content (% by weight) |
|---|---|
| Extract of red ginseng | 20 |
| Saturated lecithin | 4 |
| Phytosteryl/behenyl/octyldodecyl lauroyl glutamate | 3 |
| Xylitol | 40 |
| Distilled water | 33 |
| Total amount | 100 |

Preparation Example 11: Preparation of Nanoemulsion Containing Natural Product A nanoemulsion was prepared by the same method as described in Preparation Example 2 except that the constitutional composition of Table 10 was used.

TABLE 10

| Ingredient | Content (% by weight) |
|---|---|
| Extract of fruit of *Dioscorea polystachya* | 20 |
| Saturated lecithin | 1 |
| Phytosteryl/behenyl/octyldodecyl lauroyl glutamate | 1 |
| Glycerin | 5 |
| Distilled water | 73 |
| Total amount | 100 |

Example 1: Preparation of Complex of Nanoemulsion Containing Moisturizer and DS-LDH According to the constitutional composition of Table 11, two ingredients were introduced to a beaker and mixed with a disper mixer at 3,000 rpm for 10-20 minutes to obtain a complex of nanoemulsion containing moisturizer and DS-LDH.

TABLE 11

| Ingredient | Content (% by weight) |
|---|---|
| Nanoemulsion of Preparation Example 2 | 50 |
| DS-LDH | 50 |
| Total amount | 100 |

Example 2: Preparation of Complex of Nanoemulsion Containing Vitamin and DS-LDH According to the constitutional composition of Table 12, two ingredients were introduced to a beaker and mixed with a disper mixer at 3,000 rpm for 10-20 minutes to obtain a complex of nanoemulsion containing vitamin and DS-LDH.

TABLE 12

| Ingredient | Content (% by weight) |
|---|---|
| Nanoemulsion of Preparation Example 6 | 50 |
| DS-LDH | 50 |
| Total amount | 100 |

Comparative Example: Preparation of General Nanoemulsion Containing Vitamin

According to the constitutional composition of Table 13, ingredients were introduced to a vessel, dissolved at 50° C. and mixed for 5 minutes by the use of a homo mixer. The resulting mixture was continuously passed five (5) times through a high-pressure microfluidizer at 800 bar, followed by cooling and deaeration to obtain a nanoemulsion.

TABLE 13

| Ingredient | Content (% by weight) |
|---|---|
| Coenzyme $Q_{10}$ | 5 |
| Lecithin | 5 |
| Glycerin | 40 |
| Olive oil | 20 |
| Distilled water | 30 |
| Total amount | 100 |

Example 3: Preparation of Toner Containing Complex of Nanoemulsion and DS-LDH

A toner containing a complex of nanoemulsion and DS-LDH was prepared according to the constitutional composition of Table 14.

TABLE 14

| Ingredient | Content (% by weight) |
|---|---|
| Complex of nanoemulsion and DS-LDH of Example 1 | 3 |
| 1,3-Butylene glycol | 7 |
| PEG-1500 | 3 |
| Hyaluronic acid | 1 |
| Polyglutamic acid | 2 |
| Distilled water | 84 |
| Total amount | 100 |

Example 4: Preparation of Lotion Containing Complex of Nanoemulsion and DS-LDH

A lotion containing a complex of nanoemulsion and DS-LDH was prepared according to the constitutional composition of Table 15.

TABLE 15

| Ingredient | Content (% by weight) |
|---|---|
| Complex of nanoemulsion and DS-LDH of Example 1 | 10 |
| Polysorbate 80 | 3 |
| Cetearyl alcohol | 0.5 |
| Octyl palmitate | 3 |
| Capric/caprylic triglyceride | 4 |
| Glycerin | 5 |
| Carbopol | 0.2 |
| Silicone oil | 4 |
| Distilled water | 70.3 |
| Total amount | 100 |

Example 5: Preparation of Body Lotion Containing Complex of Nanoemulsion and DS-LDH A body lotion containing a complex of nanoemulsion and DS-LDH was prepared according to the constitutional composition of Table 16.

TABLE 16

| Ingredient | Content (% by weight) |
|---|---|
| Complex of nanoemulsion and DS-LDH of Example 1 | 5 |
| Polyglyceryl-3 methylglucose distearate | 3 |
| Squalane | 3 |
| Sunflower seed oil | 5 |
| Octyl palmitate | 4 |
| Capric/caprylic triglyceride | 2 |
| Glycerin | 8 |
| Distilled water | 70 |
| Total amount | 100 |

Example 6: Preparation of Cream Containing Complex of Nanoemulsion and DS-LDH

A cream containing a complex of nanoemulsion and DS-LDH was prepared according to the constitutional composition of Table 17.

TABLE 17

| Ingredient | Content (% by weight) |
|---|---|
| Complex of nanoemulsion and DS-LDH of Example 1 | 10 |
| Saturated lecithin | 5 |
| Cetearyl alcohol | 1.5 |
| Squalane | 6 |
| Olive oil | 3 |
| Dimethicone oil | 2 |
| Glycerin | 8 |
| Carbopol | 0.36 |
| Distilled water | 64.14 |
| Total amount | 100 |

Example 7: Preparation of Essence Containing Complex of Nanoemulsion and DS-LDH

An essence containing a complex of nanoemulsion and DS-LDH was prepared according to the constitutional composition of Table 18.

TABLE 18

| Ingredient | Content (% by weight) |
| --- | --- |
| Complex of nanoemulsion and DS-LDH of Example 1 | 30 |
| Polyglutamic acid | 1 |
| Glycerin | 7 |
| PEG-1500 | 3 |
| Allantoin | 0.1 |
| Sodium EDTA | 0.05 |
| Calcium hydroxide | 0.03 |
| Carbopol | 0.4 |
| Distilled water | 58.42 |
| Total amount | 100 |

Experimental Example 1: Analysis of LDH

Scanning electron microscope (SEM) photographs were taken by the use of S-4800 (Hitachi High-Technologies Corporation, Japan), and high resolution transmission electron microscope (HRTEM) photographs were taken by the use of JEM-3010 (JEOL Ltd., Japan). Ultraviolet-visible spectra (UV/Vis spectra) were obtained by the use of Lamda 1050 (PerkinElmer Inc., USA), and X-ray diffraction (XRD) patterns were obtained by the use of D5000 (Siemens, Germany). The results of Fourier-transform infrared spectra (FT-IR) were obtained by the use of IRAffinity-1 (Shimadzu Corporation, Japan) equipped with attenuated total reflectance (ATR) mode over a wavenumber region of 400-4000 $cm^{-1}$. Zeta potential was measured by the use of Zetasizer nano ZS (Malvern Instruments, UK), and thermogravimetric analysis (TGA) was carried out by the use of TGA 4000 (PerkinElmer Inc., USA) under nitrogen atmosphere.

Figure 3A:
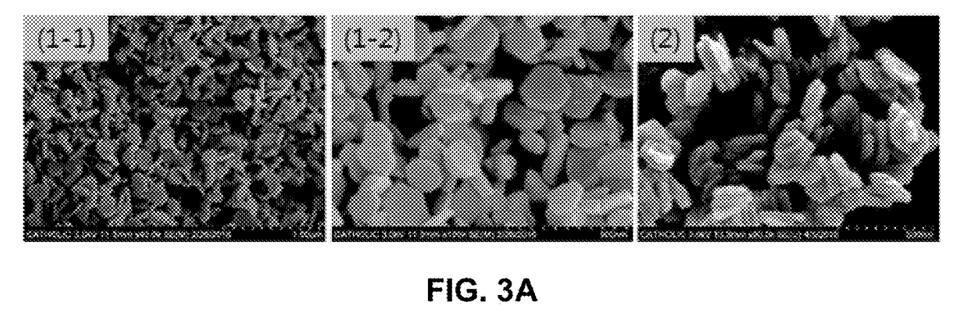
FIG. 3A is electron microscopy photographs of (1) ZnAl-carbonate LDH (c-LDH) and (2) ZnAl-carbonate LDH in which the surface is treated with stearic acid (SA-LDH)
Figure 3B:
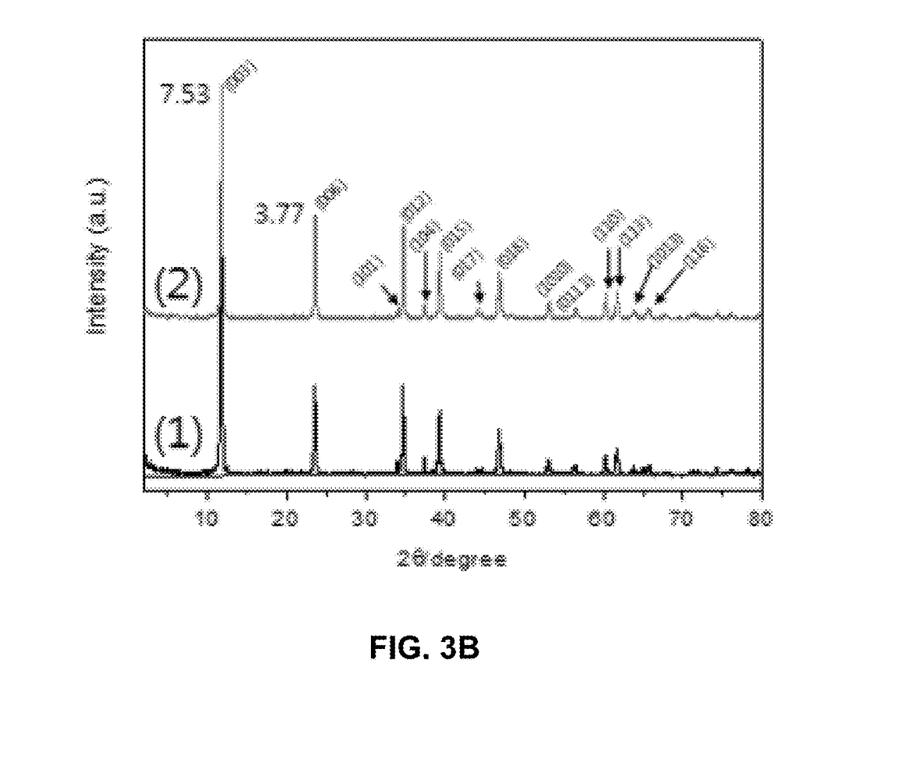
FIG. 3B represents XRD (x-ray diffraction) pattern.
Figure 3C:
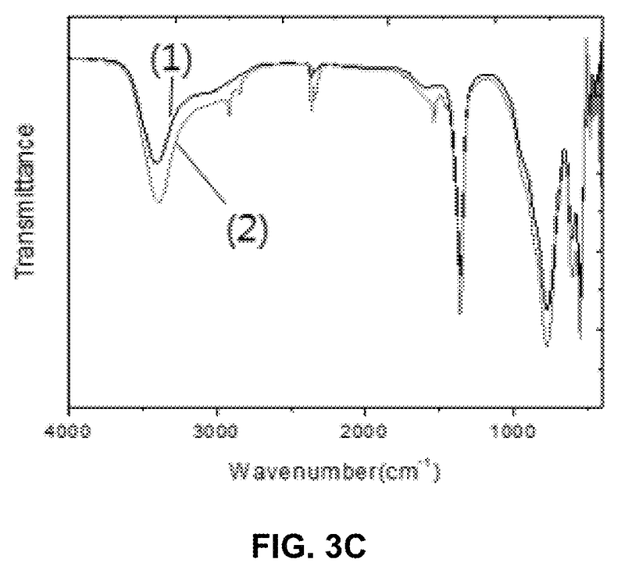
FIG. 3C is a result of FT-IR spectrum.

The results about morphology and size of particles, the internal structure and chemical functional groups of the surface of c-LDH and SA-LDH synthesized in Preparation Examples 1-1 and 1-2, respectively, are represented in FIG. 3. c-LDH has the size of about 100-200 nm and the thickness of about 50 nm. It was confirmed that XRD patterns thereof are similar to hydrotalcite having the layered structure. Sharp and symmetrical peak shapes of XRD patterns show excellent crystalline property of c-LDH. It could be known that the crystal lattice constant a is about 0.306 nm by the use of the relationship of a=2d(110) at (110) peak near 60°. In addition, it could be known that the crystal lattice constant c is about 2.26 nm because it is applicable to three times of interlayer distance (0.753 nm) corresponding to (003) peak. Considering that the thickness of a single layer of general LDH is 0.48 nm, it could be known that the interlayer distance in which anions is located is about 0.27 nm. It was confirmed that the above results of the synthesis correspond very well with values in articles that have already been reported. Chemical functional groups of c-LDH were confirmed by FT-IR analysis. The broad absorption band observed at about 3400 $cm^{-1}$ region is due to numerous hydroxyl groups and surface-adsorbed water molecules, and very strong absorption band observed at about 1350 $cm^{-1}$ region is due to C—O vibration of carbonate which is interlayer anion. The bending vibration of water molecules between LDH layers is observed at about 1630 $cm^{-1}$ region. Generally, LDH materials show infrared absorption due to vibration of metal and oxygen below 800 $cm^{-1}$ region. From the FT-IR result shown in (1) of FIG. 3C, it was confirmed that this is very similar with that shown in LDH materials of typical carbonate form. From the electron microscopy photograph of (2) of FIG. 3C and the XRD result of (2) of FIG. 3B, it was confirmed that a hydrophobic organic acid-treated SA-LDH has a layered structure similar to c-LDH, and its morphology and size are not changed after surface treatment. From the FT-IR result shown in (2) of FIG. 3C, strong C—H absorption vibration of hydrophobic alkyl chain was observed near 2800-3000 $cm^{-1}$ region. Consequentially, it was confirmed that the hydrophobic organic acid treatment is a way to effectively adsorb a hydrophobic organic acid onto the surface of LDH without affecting the internal structure, size and morphology of c-LDH. In addition, from (2) of FIG. 3A, it could be known that particles have face-to-face contacts and partially agglomerate by strong interaction of hydrophobically modified surface of particles.

Figure 4A:
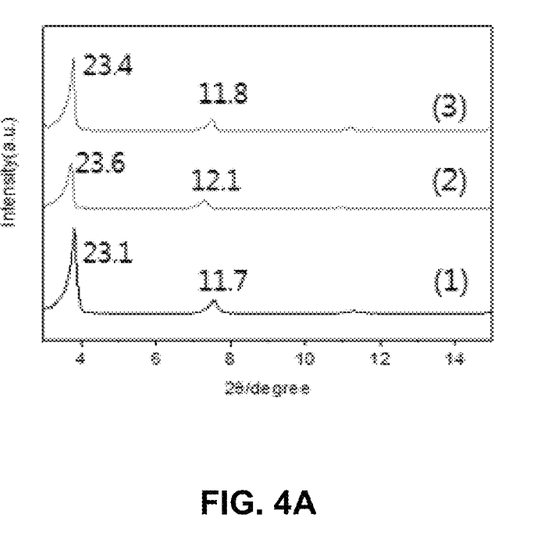
FIG. 4A is XRD (x-ray diffraction) patterns of dodecyl sulfate-modified layered double hydroxides (DS-LDHs) synthesized by (1) a hydrothermal method, (2) a convection circulation method and (3) an ultrasonic method.
Figure 4B:
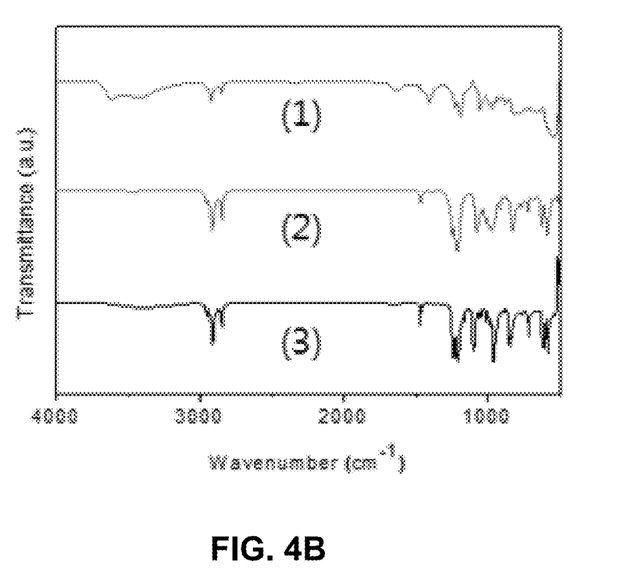
FIG. 4B is results of FT-IR spectrum and FIG. 4C is electron microscopy photographs.
Figure 4C:
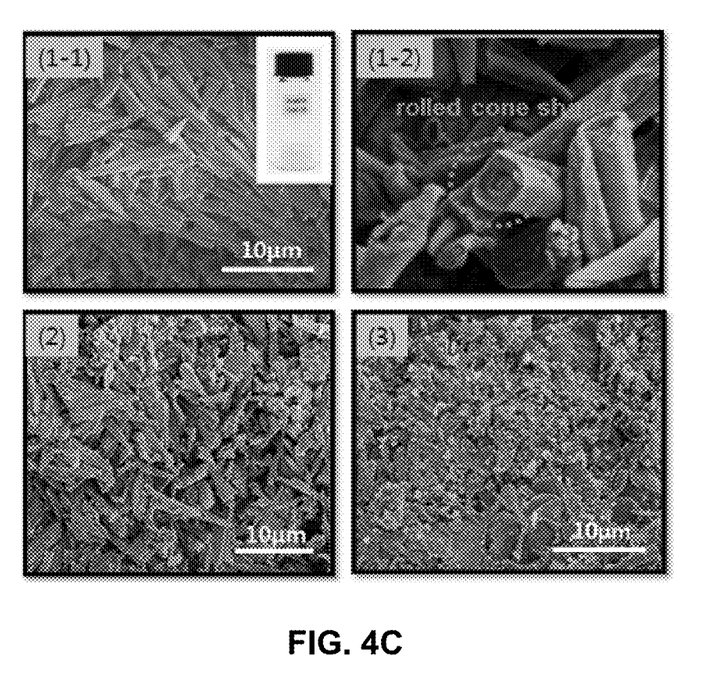

The results about morphology and size of particles, the internal structure and chemical functional groups of the surface of DS-LDH synthesized by a hydrothermal method, a convection circulation method and an ultrasonic method are represented in FIG. 4. From the XRD analysis results of FIG. 4A, it could be known that all DS-LDHs synthesized by three methods have a layered structure. Specifically, the strong peak of angle of diffraction about 3.7° represents interlayer distance, and it was confirmed that all of them have about 2.3 nm of interlayer distance. In this case, because dodecyl sulfate anions are located in the interlayer regions of LDH, it is assumed that it has very large interlayer distance as compared with c-LDH. The presence of dodecyl sulfate ion of DS-LDH was also confirmed by FT-IR analysis. FIG. 4B represents FT-IR spectrums of DS-LDHs synthesized by three methods. As similar to c-LDH, alkyl chain C—H vibration was confirmed near the 2800-3000 $cm^{-1}$ region as well as LDH-intrinsic absorption bands corresponding to O—H vibration, bending vibration of water molecules and vibration of metal-oxygen. From the results of electron microscopy of FIG. 4c, morphology and size of DS-LDH particles could be confirmed. All samples are shaped like corn, and it could be known that the size of particles varies depending on the synthesis method. Specifically, DS-LDH synthesized by a hydrothermal method has the largest size of particles and clear edge. As can be seen from the magnified electron microscopy photograph of (1-1) of FIG. 4C, it could be known that the tabular structure is rolled to form a shape like corn.

Experimental Example 2: Measurement of Particle Size Distribution

Figure 5:
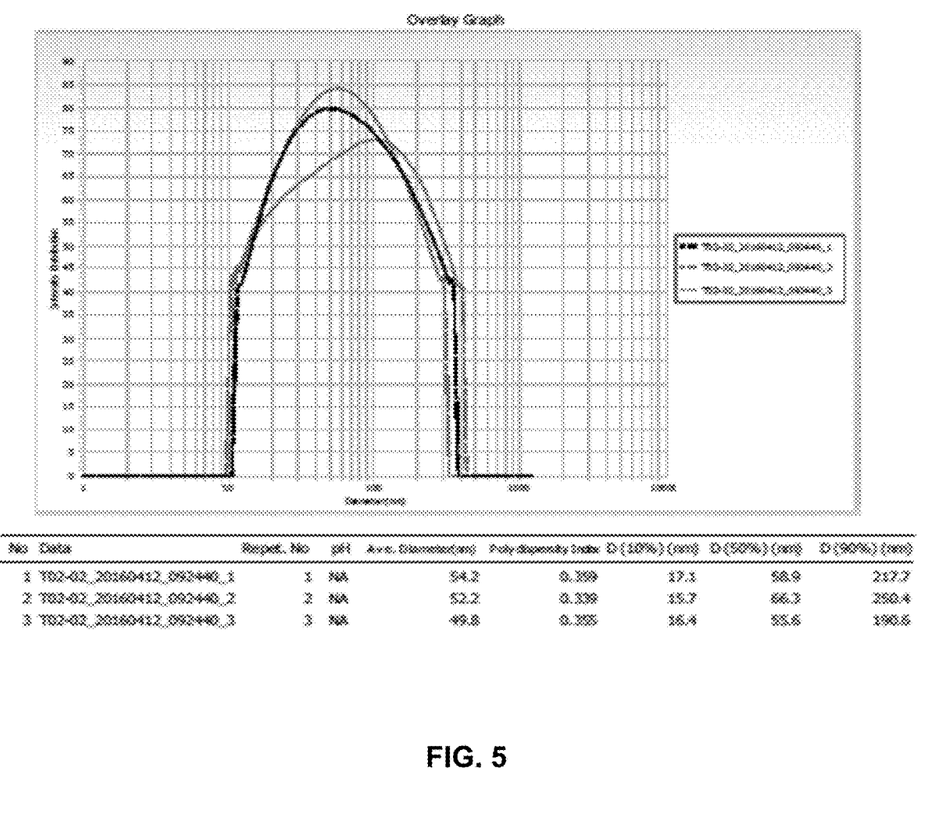
FIG. 5 is a result of measuring the diameter of the nanoemulsion by the use of Photal ELS-Z.
Figure 6:
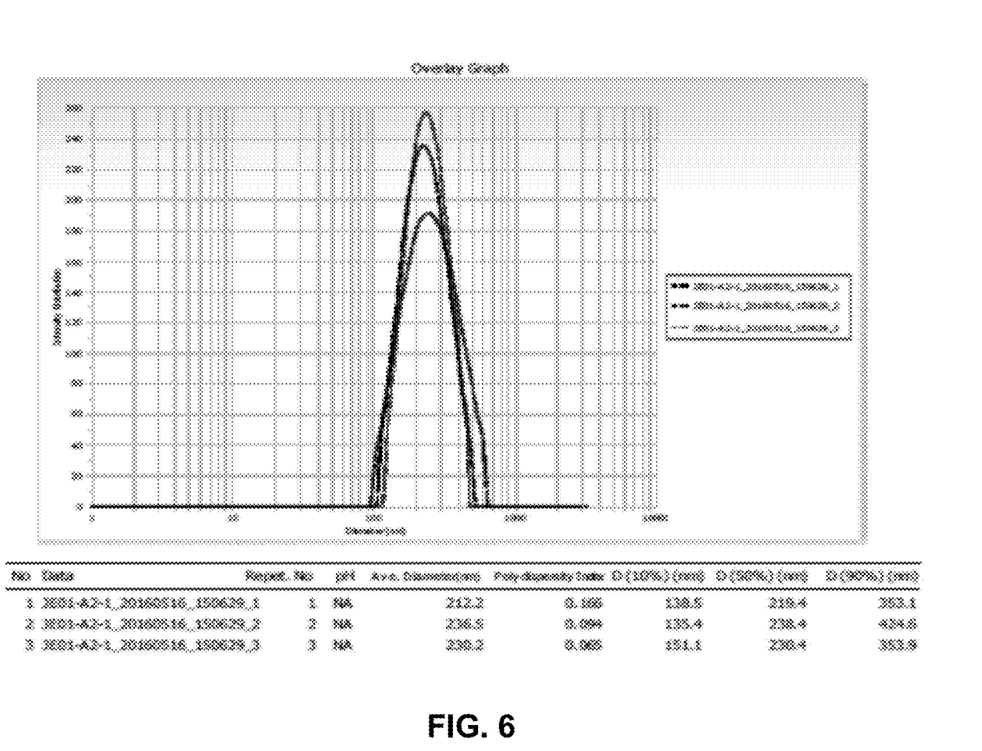
FIG. 6 is a result of measuring the diameter of the complex of nanoemulsion and DS-LDH by the use of Photal ELS-Z.

The particle size distributions of the nanoemulsion prepared in Preparation Example 6 and the complex of nanoemulsion containing vitamin and DS-LDH prepared in Example 2 were measured by the use of Photal ELS-Z, and the results are represented in FIGS. 5 and 6, respectively. From the results of the measurement, it can be known that the average particle sizes are 52.1 nm and 226 nm, respectively.

Experimental Example 3: Cryo-Electron Microscopy

Figure 7:
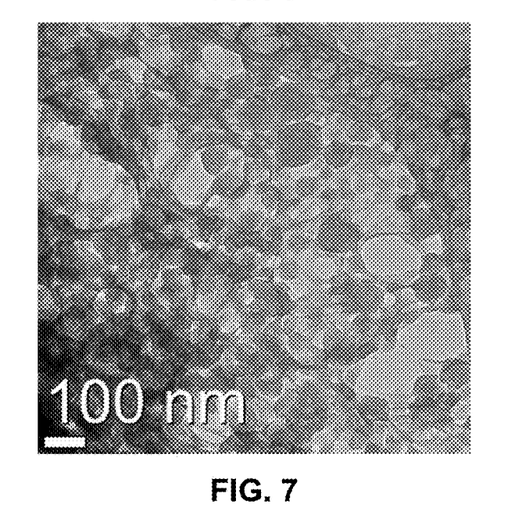
FIG. 7 is a cryo-electron microscopy photograph of the nanoemulsion.
Figure 8:
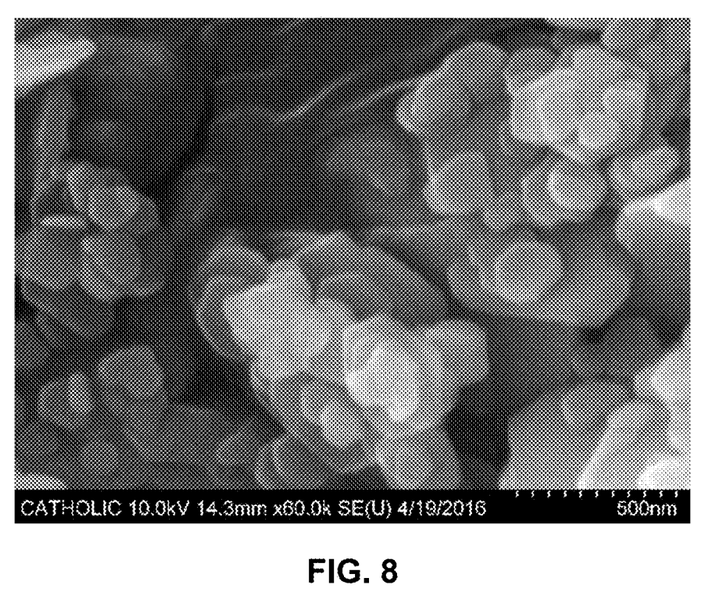
FIG. 8 is a cryo-electron microscopy photograph of the complex of nanoemulsion and DS-LDH.

Photographs of the nanoemulsion prepared in Preparation Example 6 and the complex of nanoemulsion containing vitamin and DS-LDH prepared in Example 2 were taken. Due to very fine particle size, it was impossible to take photographs by a general optical microscope. Therefore, cryo-electron microscopy photographs (JEM 1010, JEOL Ltd., Japan) were taken (FIGS. 7 and 8). From FIG. 8, it can be known that the complex of nanoemulsion and DS-LDH is well formed.

Experimental Example 4: Test for Promoting Transdermal Absorption

An 8-week-old female hairless guinea pig (strain IAF/HA-hrBR) was used. The abdominal skin of the guinea pig was cut and mounted to a Franz-type diffusion cell (Lab Fine Instruments, Korea). 50 mM phosphate buffer (pH 7.4, 0.1M NaCl) was added to a receptor cell (5 ml) of the Franz-type diffusion cell. A diffusion cell was then mixed and diffused at 600 rpm, 32° C., and 50 µl of the complex of nanoemulsion containing vitamin and DS-LDH prepared in Example 2 and the emulsion of the Comparative Example, respectively, were added to donor cells. Absorption and diffusion were carried out according to the predetermined time, and the area of the skin where the absorption and diffusion were carried out was 0.64 cm². After finishing the absorption and diffusion of the active ingredient, the residues-which were not absorbed and remained on the skin-were cleaned with dried Kimwipes™ or 10 ml of ethanol. The skin in which the active ingredient was absorbed and diffused was homogenized by the use of a tip-type homogenizer, and coenzyme $Q_{10}$ absorbed into the skin was then extracted with 4 ml of dichloromethane. The extract was then filtrated with a 0.45 µm nylon membrane filter. The content was measured by high-performance liquid chromatography with the following conditions, and the results are represented in Table 19.

TABLE 19

| | Transdermal absorption (µg) | Rate of increase |
|---|---|---|
| Comparative Example | 0.123 | — |
| Example 2 | 1.587 | 13-fold |

A) Column: C18 (4.6 × 200 mm, 5 µm)
B) Mobile phase: methanol:hexane = 2:1
C) Flow rate: 0.8 ml/min
D) Detector: UV 275 nm As can be seen from Table 19, the composition for transdermal delivery of the present invention can efficiently deliver coenzyme $Q_{10}$ into the skin.

What is claimed is:

1. A composition for transdermal delivery comprising:
   1) a nanoemulsion consisting of an active ingredient, saturated lecithin, phytosteryl/behenyl/octyldodecyl lauroyl glutamate, a polyol and water; and
   2) a modified layered double hydroxide,
   wherein the polyol is one or more selected from the group consisting of glycerin, xylitol, erythritol, fructose, lactose, mannitol, glucose, sucrose, maltose, maltitol, and ethylene glycol.

2. The composition for transdermal delivery according to claim 1, wherein the nanoemulsion consists of 1 to 40% by weight of active ingredient, 0.1 to 20% by weight of saturated lecithin, 0.1 to 20% by weight of phytosteryl/behenyl/octyldodecyl lauroyl glutamate, 2 to 70% by weight of polyol and 10 to 80% by weight of water.

3. The composition for transdermal delivery according to claim 2, wherein the nanoemulsion consists of 5 to 30% by weight of active ingredient, 0.2 to 15% by weight of saturated lecithin, 0.2 to 15% by weight of phytosteryl/behenyl/octyldodecyl lauroyl glutamate, 3 to 65% by weight of polyol and 15 to 75% by weight of water.

4. The composition for transdermal delivery according to claim 1, wherein the active ingredient is one or more selected from the group consisting of a moisturizer, a whitening agent, an anti-wrinkle agent, a UV blocking agent, a hair growth promoter, vitamin or a derivative thereof, amino acid or peptide, an anti-inflammatory agent, an acne therapeutic agent, a microbicide, female hormone, a keratolytic agent and a natural product.

5. The composition for transdermal delivery according to claim 1, wherein the modified layered double hydroxide is modified with dodecyl sulfate.

6. The composition for transdermal delivery according to claim 5, wherein the dodecyl sulfate-modified layered double hydroxide is in the form of nanosheet.

7. The composition for transdermal delivery according to claim 1, wherein the layered double hydroxide of the modified layered double hydroxide has the following formula:

$$[M^{2+}_{1-x}M^{3+}_{x}(OH)_2]^{x+}(A^{n-})_{x/n}\cdot mH_2O$$

wherein
$M^{2+}$ and $M^{3+}$ are metal cations,
$A^{n-}$ is anion,
$0.2 \leq x \leq 0.33$,
m is 0.5 to 4, and
n is 1 or 2.

8. The composition for transdermal delivery according to claim 7, wherein $M^{2+}$ is $Ca^{2+}$, $Mg^{2+}$, $Zn^{2+}$, $Ni^{2+}$, $Mn^{2+}$, $Co^{2+}$ or $Fe^{2+}$; $M^{3+}$ is $Al^{3+}$, $Cr^{3+}$, $Mn^{3+}$, $Fe^{3+}$, $Ga^{3+}$, $Co^{3+}$ or $Ni^{3+}$; and $A^{n-}$ is $OH^-$, $F^-$, $Cl^-$, $Br^-$, $I^-$, $NO_3^-$, $CO_3^{2-}$ or $SO_4^{2-}$.

9. The composition for transdermal delivery according to claim 1, which comprises 30 to 70% by weight of the nanoemulsion and 30 to 70% by weight of the modified layered double hydroxide.

10. The composition for transdermal delivery according to claim 9, which comprises 40 to 60% by weight of the nanoemulsion and 40 to 60% by weight of the modified layered double hydroxide.

11. A method for preparing a composition for transdermal delivery according to claim 1, comprising:
   i) mixing an active ingredient, saturated lecithin, phytosteryl/behenyl/octyldodecyl lauroyl glutamate, a polyol and water, and preparing a nanoemulsion; and
   ii) mixing the nanoemulsion prepared in step (i) and a modified layered double hydroxide to obtain a complex,
   wherein the polyol is one or more selected from the group consisting of glycerin, xylitol, erythritol, fructose, lactose, mannitol, glucose, sucrose, maltose, maltitol and ethylene glycol.

12. The method for preparing a composition for transdermal delivery according to claim 11, wherein 1 to 40% by weight of active ingredient, 0.1 to 20% by weight of saturated lecithin, 0.1 to 20% by weight of phytosteryl/behenyl/octyldodecyl lauroyl glutamate, 2 to 70% by weight of polyol and 10 to 80% by weight of water are mixed in step (i).

13. The method for preparing a composition for transdermal delivery according to claim 11, wherein the active ingredient is one or more selected from the group consisting of a moisturizer, a whitening agent, an anti-wrinkle agent, a UV blocking agent, a hair growth promoter, vitamin or a derivative thereof, amino acid or peptide, an anti-inflammatory agent, an acne therapeutic agent, a microbicide, female hormone, a keratolytic agent and a natural product.

14. The method for preparing a composition for transdermal delivery according to claim 11, wherein the modified layered double hydroxide is modified with dodecyl sulfate.

15. The method for preparing a composition for transdermal delivery according to claim 11, wherein 30 to 70% by weight of the nanoemulsion and 30 to 70% by weight of the modified layered double hydroxide are mixed in step (ii).

16. A composition for transdermal delivery comprising:
1) a nanoemulsion consisting of an active ingredient, saturated lecithin, phytosteryl/behenyl/octyldodecyl lauroyl glutamate, a polyol, water, and vegetable oil; and
2) a modified layered double hydroxide,
wherein the polyol is one or more selected from the group consisting of glycerin, xylitol, erythritol, fructose, lactose, mannitol, glucose, sucrose, maltose, maltitol, and ethylene glycol.

17. The composition for transdermal delivery according to claim 16, wherein the nanoemulsion consists of 1 to 40% by weight of active ingredient, 0.1 to 20% by weight of saturated lecithin, 0.1 to 20% by weight of phytosteryl/behenyl/octyldodecyl lauroyl glutamate, 2 to 70% by weight of polyol, 10 to 80% by weight of water and 10 to 30% by weight of vegetable oil.

18. The composition for transdermal delivery according to claim 16, wherein the vegetable oil is selected from the group consisting of olive oil, macadamia oil, sunflower seed oil, *camellia* oil, castor oil, jojoba oil, almond oil, apricot kernel oil, green tea oil, meadowfoam seed oil, argan oil and a mixture thereof.

* * * * *